United States Patent [19]
Liotta et al.

[11] Patent Number: 5,843,657
[45] Date of Patent: Dec. 1, 1998

[54] ISOLATION OF CELLULAR MATERIAL UNDER MICROSCOPIC VISUALIZATION

[75] Inventors: Lance A. Liotta, Potomac; Michael E. Buck, Bethesda, both of Md.; Rhonda Weiss, Washington, D.C.; Zhongping Zhuang, Bethesda, Md.

[73] Assignee: The United States of America as represented by the Department of Health and Human Services, Washington, D.C.

[21] Appl. No.: 544,388

[22] Filed: Oct. 10, 1995

Related U.S. Application Data

[63] Continuation-in-part of Ser. No. 203,780, Mar. 1, 1994.
[51] Int. Cl.$^6$ .............................. A01N 1/02; A01N 1/00; A01N 3/00
[52] U.S. Cl. ...................... 435/6; 435/1; 156/57; 436/174; 436/175; 436/177; 436/63
[58] Field of Search ............................ 435/1, 6; 156/57; 436/63, 174, 175, 177

[56] References Cited

U.S. PATENT DOCUMENTS

| | | | |
|---|---|---|---|
| 2,659,981 | 8/1953 | Beckham | 33/174 |
| 3,989,591 | 11/1976 | Liotta | 195/1.8 |
| 4,012,475 | 3/1977 | Kindel | 264/28 |
| 4,144,760 | 3/1979 | Schlueter et al. | 73/425 |
| 4,366,245 | 12/1982 | Lalonde | 435/30 |
| 4,485,706 | 12/1984 | Disharoon | 83/42 |
| 4,500,509 | 2/1985 | Kass | 424/3 |
| 4,545,831 | 10/1985 | Ornstein | 156/57 |
| 4,619,899 | 10/1986 | Nikitin | 435/287 |
| 4,628,026 | 12/1986 | Gardell et al. | 435/7 |
| 4,635,791 | 1/1987 | Jackson et al. | 206/210 |
| 4,647,543 | 3/1987 | Stocker | 436/174 |
| 4,649,109 | 3/1987 | Perlman | 435/30 |
| 4,741,043 | 4/1988 | Bacus | 382/6 |
| 4,749,868 | 6/1988 | Hatanaka et al. | 250/443.1 |
| 4,767,717 | 8/1988 | Baisden | 436/64 |
| 4,907,158 | 3/1990 | Ketter et al. | 364/413.01 |
| 4,960,224 | 10/1990 | Boenisch | 206/456 |
| 5,023,172 | 6/1991 | Djordjevic | 435/29 |
| 5,137,710 | 8/1992 | Smalley et al. | 424/3 |
| 5,218,645 | 6/1993 | Bacus | 382/6 |
| 5,225,750 | 7/1993 | Higuchi et al. | 318/280 |
| 5,234,522 | 8/1993 | Bacus et al. | 364/497 |
| 5,252,487 | 10/1993 | Bacus et al. | 436/63 |
| 5,264,341 | 11/1993 | Maciak et al. | 435/7.21 |
| 5,281,517 | 1/1994 | Bacus et al. | 435/6 |
| 5,428,690 | 6/1995 | Bacus et al. | 382/128 |
| 5,451,500 | 9/1995 | Stapleton | 435/6 |

FOREIGN PATENT DOCUMENTS

| | | |
|---|---|---|
| 0539888 | 10/1992 | European Pat. Off. . |
| 539888 A1 | 5/1993 | European Pat. Off. . |
| 2659981 | 3/1990 | France . |
| 1074885 | 7/1955 | Germany . |

OTHER PUBLICATIONS

Vogles et al, New Eng. J. Med., Jul. 14, 1988, vol. 319(2) pp. 75–79.

*Primary Examiner*—James C. Housel
*Assistant Examiner*—Ginny Allen Portner
*Attorney, Agent, or Firm*—Lowe, Price, LeBlanc & Becker

[57] ABSTRACT

A method of microdissection which involves: forming an image field of cells of the tissue sample utilizing a microscope, identifying at least one zone of cells of interest from the image field of cells which at least one zone of cells of interest includes different types of cells than adjacent zones of cells, and extracting the at least one zone of cells of interest from the tissue sample. The extraction is achieved by contacting the tissue sample with a transfer surface that can be selectively activated so that regions thereof adhere to the zone of cells of interest to be extracted. The transfer surface includes an activatable adhesive layer which provides chemical or electrostatic adherence to the selected regions of the tissue sample. After the transfer surface is activated the transfer surface and tissue sample are separated. During separation the zone of cells of interest remains adhered to the transfer surface and is thus separated from the tissue sample.

16 Claims, 8 Drawing Sheets

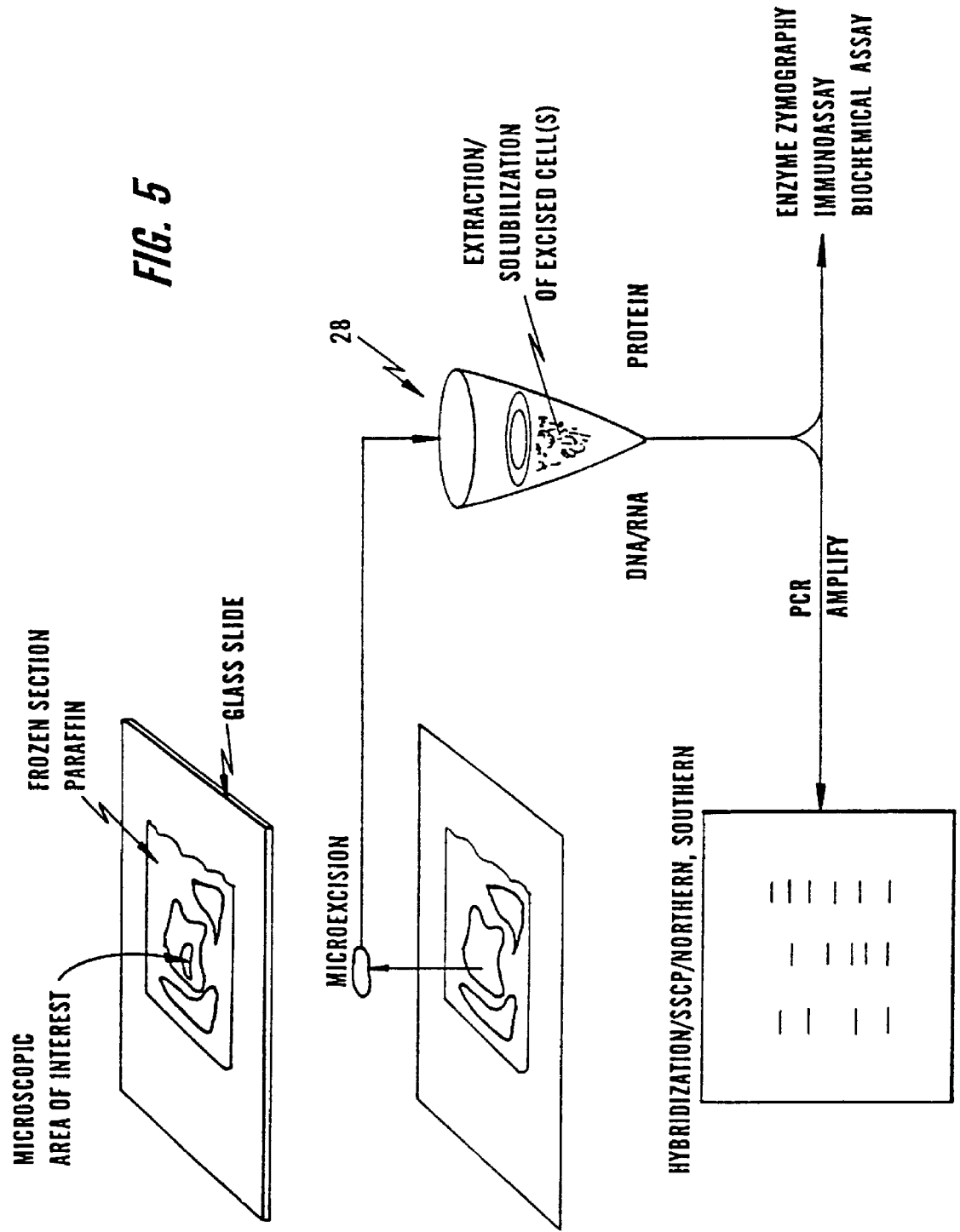

ISOLATION OF CELLULAR MATERIAL UNDER MICROSCOPIC VISUALIZATION

RELATED APPLICATION

The present application is a continuation-in-part of U.S. patent application Ser. No. 08/203,780, filed Mar. 1, 1994, pending.

TECHNICAL FIELD

The present invention relates to methods and devices for the analysis of cellular samples. More particularly, the present invention relates to methods and devices for the microdissection and analysis of cellular samples which may be used in combination with a number of different technologies that allow for analysis of enzymes, MRNA and DNA from pure populations or subpopulations of particular cell types.

BACKGROUND ART

Many diseases are now understood at the molecular and genetic level. Analysis of such molecules is important for disease diagnosis and prognosis. Previous methods for direct extraction of cellular tissue material from a tissue sample are limited because the extraction reflects only the average content of disease associated markers. In reality, tissues are very heterogeneous, and the most diagnostic portions of the tissue may be confined to a few hundred cells or less in a lesion.

Normal tissue samples contain a variety of cell types surrounding and adjacent to the pre-invasive and invasive tumor cells. A region of the tumor tissue subject to biopsy and diagnosis as small as 1.0 mm can contain normal epithelium, pre-invasive stages of carcinoma, in-situ carcinoma, invasive carcinoma, and inflammatory areas. Consequently, routine scraping and cutting methods will gather all of these types of cells, and hence, loss of an allele will be masked by presence of a normal copy of the allele in the contaminating non-malignant cells. Existing methods for cutting away or masking a portion of tissue do not have the needed resolution. Hence the analysis of genetic results by those previous are always plagued by contaminating alleles from normal cells, undesired cells or vascular cells.

The molecular study of human tumors is currently limited by the techniques and model systems available for their characterization. Studies to quantitatively or qualitatively asses proteins or nucleic acid expression in human tumor cells are compromised by the diverse cell populations present in bulk tumor specimens. Histologic fields of invasive tumor typically show a number of cell types including tumor cells, stromal cells, endothelial cells, normal epithelial cells and inflammatory cells. Since the tumor cells are often a relatively small percentage of the total cell population it is difficult to interpret the significance of net protein or nucleic acid alterations in these specimens.

The processes of tumor invasion and metastasis depend upon increased proteolytic activity of invading tumor cells. Matrix metalloproteinases, cathepsins B, D, and L, and plasminogen activator have been implicated in the metastatic cascade. Cathepsin D has been suggested to be an independent marker of prognosis in breast cancer. Several lines of correlation evidence support the concept that proteases are important in tumor invasion including: increased protease activity and/or altered subcellular distribution of proteases in highly metastatic tumor cell lines, increased protease expression in invasive human tumors as determined by both immunohistochemistry and assays of tumor tissue homogenates, and increased MRNA levels in human tumors. All of these techniques have generated important information regarding protease expression in human tumors, however, they have not provided definitive evidence that proteases are up-regulated in specific regions where tumor invasion is occurring.

Studies of human tumor cells in culture do not account for the complex interactions of the tumor cells with host cells and extracellular matrix, and how they may regulate tumor cell protease productivity or activation. Immunohistochemical staining allows one to examine enzyme distribution in regions of tumor invasion, however, results vary with tissue fixation and antibody-antigen affinity, and provide only a semi-quantitative assessment of protein levels. Furthermore, quantitative interpretation of staining results is complicated by the variability of staining patterns within tissue sections, subjective evaluation of staining intensity, and the difficulty in interpreting the significance of stromal staining. In addition, many antibodies utilized in the study of proteases do not differentiate pro-enzyme from active enzyme species. Assays of enzyme or MRNA levels from homogenates of human tumors does not account for either the mixed population of cells within the specimens, or the concomitant pathophysiologic processes which may be occur in the tissue.

Human tumors accumulate genetic abnormalities as they develop from a single transformed cell to invasive and metastatic carcinoma. Identification and characterization of the genes which are mutated, lost or abnormally regulated can provide important insights for cancer diagnosis, prognosis, and therapy. Furthermore, identification of such genetic lesions may facilitate early diagnosis by definitive identification of premalignant lesions so they can be treated before they progress to invasive cancer.

A general dictum of cancer progression states that cells can be transformed after acquiring two separate alterations in the tumor suppressor gene. Subsequent tumors progress stepwise from dysplastic lesions to in-situ, to invasive and metastatic neoplasms. In-situ carcinomas are frequently observed arising in association with a spectrum of epithelial hyperplasias and larger invasive tumors are often associated with regions of carcinoma in-situ at the tumor periphery.

Pathologists have historically interpreted a side-by-side association of atypical hyperplasia, in-situ carcinoma, and invasive tumors as evidence of a cause and effect relationship among the entities. However, little direct evidence existed previously which supports this model.

Prior methods of study have not allowed investigators to specifically examine genetic alterations in pre-invasive lesions. The present invention provides a novel improved means to specifically examine genetic alterations in pre-invasive lesions of common epithelial tumors such as breast and prostate carcinoma. In particular the present invention permits the microsampling of five or less cells with RNA and DNA extraction of the sampled cells. This method has been demonstrated to be extremely sensitive and to surpass previous and current technologies by more than two orders of magnitude. It has allowed the sensitive detection of loss of heterozygosity in early pre-invasive lesions being a gateway to the discovery of a new genetic loci on chromosome 11 for breast cancer and a new genetic loci on chromosome 8 for prostate carcinoma.

DISCLOSURE OF THE INVENTION

It is according one object of the present invention to provide a method of identifying specific cells in cellular tissue sample.

Another object of the present invention is to provide a method of direct extraction of specific cells from a cellular tissue sample.

It is a further object of the present invention to provide an automated method of identifying specific cells in cellular tissue sample.

A further object of the present invention is to provide an automated method of direct extraction of specific cells from a cellular tissue sample.

A still further object of the present invention is to provide a method of obtaining pure cell populations from a cellular tissue samples.

According to these and further objects of the present invention which will become apparent as the description thereof proceeds, the present invention provides for a method of direct extraction of cellular material from a tissue sample which involves:

providing a tissue sample;

contacting the tissue sample with a transfer surface which can be activated to provide selective regions thereof with adhesive characteristics;

identifying at least one portion of the tissue sample which is to be extracted;

activating a region of the transfer surface which is in contact with the at least one portion of the tissue sample so that the activated region of the transfer surface adheres to the at least one portion of the tissue sample; and separating the transfer surface from the tissue sample while maintaining adhesion between the activated region of the transfer surface and the at least one portion of the tissue sample so that the at least one portion of the tissue sample is extracted from a remaining portion of the tissue sample.

BRIEF DESCRIPTION OF DRAWINGS

The present invention will be described with reference to the attached drawings which are given by way of non-limiting examples only, in which:

FIG. 5 is a functional system diagram which shows how a zone of sample tissue can be directed to an appropriate analysis protocol.

BEST MODE FOR CARRYING OUT THE INVENTION

The present invention is directed to a method of analyzing cellular material on a molecular or genetic level which involves: visualizing a field of cells in a tissue sample under a microscope, contacting an identified area with a surface which simultaneously dissolves, extracts and/or retains a cellular material of interest, and transferring the cellular material of interest to a suitable analysis system. The present invention is particularly applicable to the analysis of local tissue enzymes, antigens, DNA, RNA, and the like.

According to a preferred embodiment, the present invention is directed to adhesive transfer methods which involve microscopic visualization and transfer of cellular material to a procurement or transfer surface.

The present invention is also directed to a fully automated system whereby a tissue can be visualized on a screen, so that a precise field of cells of interest can be identified by a variety of labels, circumscribed, and then be automatically extracted and analyzed.

Figure 1:
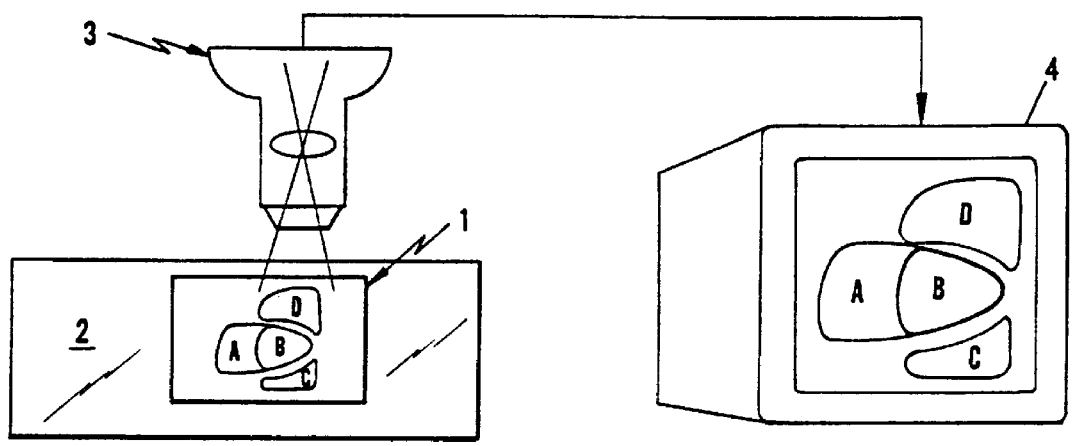
FIG. 1 is a functional system diagram which shows how a tissue sample is microscopically imaged, displayed on a display monitor, and how a region of the imaged sample is selected and identified for subsequent microdissection and analysis.

FIG. 1 is a functional system diagram which shows how a tissue sample is microscopically imaged, displayed on a display monitor, and how a region of the imaged sample is selected and identified for subsequent microdissection and analysis. As depicted in FIG. 1, a tissue sample 1 is provided on a glass slide 2 for microscopic examination and imaging. The sample tissue 1 can be fixed on the glass slide 2 according to any conventional method, including attachment to the glass slide 2 with an agarose gel, fixing the tissue sample in paraffin, etc.

The glass slide 2 having the sample tissue 1 mounted thereon is placed on the stage of a microscope. The microscope, generally indicated by reference numeral 3 receives an image of the tissue sample 1. A video camera (not shown) is connected to the microscope 3. The video camera receives the image of the sample tissue 1 from the microscope 3 and displays the image of the tissue sample on a display monitor 4.

The image of the sample tissue 1 is limited to the "field" of the microscope 3 for any given image. As indicated in FIG. 1, the field of the sample tissue image may include several zones, "A", "B", "C", and "D" of different types of cells which can be optically distinguished by utilizing a suitable dye(s) to stain the tissue sample. For exemplary purposes, FIGS. 1 and 2a–2c assume that zone "B" is the zone of cellular material of interest. The image on the display monitor 4 is used by the operator to select and identify one or more zones of the tissue sample 1 which are of interest. According to one embodiment of the present invention, after the zone(s) of interest are selected and identified, the operator manually manipulates a device to extract the identified zone(s) from the glass slide 2. The extracted zone(s) of sample material may either include an analysis sample. Otherwise, the identified and extracted zone(s) can include zones which are to discarded and the remaining zone(s) which are retained on the glass slide 2, can be later analyzed.

In addition to manual operation which is discussed in more detail below, it is possible, according to another embodiment of the present invention, to utilize the image on the display monitor 4 to select and identify a sample zone(s) whose relative position is determined utilizing a computer which receives a digitized signal of the image from the video camera (or microscope), and which receives a reference position of the stage of the microscope 3 upon which the sample is held. Such positioning detection and recognition systems are conventional in the art and can be readily applied to automate the sample preparation method of the present invention. In this automated embodiment of the invention, the computer which performs the positioning detection and recognizing can also be used to control the movement of the devices discussed below that are used to extract tissue zones, thus automating the sample removal. In addition, the image of the sample can be electronically scanned to automatically identify zones having a predetermined or relevant degree of staining, using known techniques and devices. Thus, in a preferred embodiment, a computer could be used to select and identify zones of interest and the relative position of such zones, for manipulating a device to remove such zones in an automated manner.

Figure 2A:
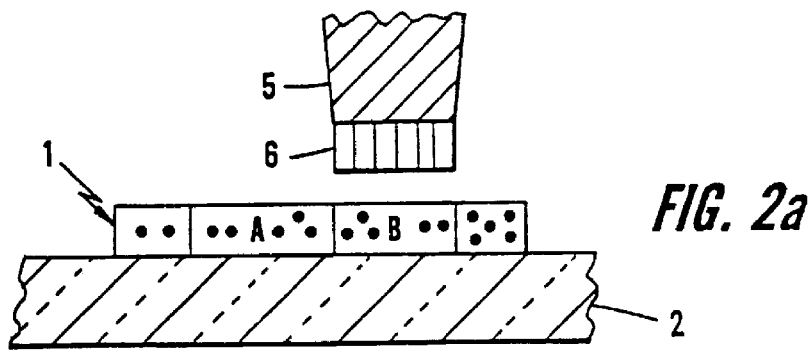
FIGS. 2a–2c are a series of functional system diagrams which show how a zone of tissue sample is extracted from the slide-mounted tissue sample according to one embodiment of-the present invention.
Figure 2B:
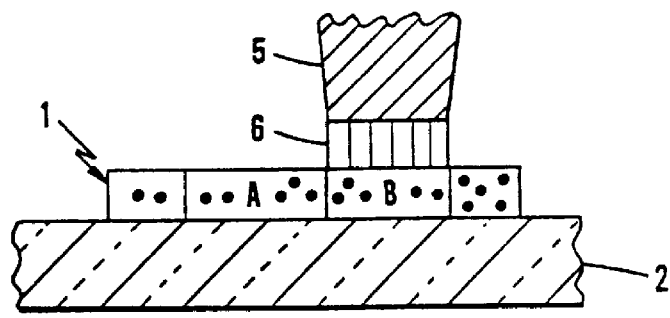
Figure 2C:
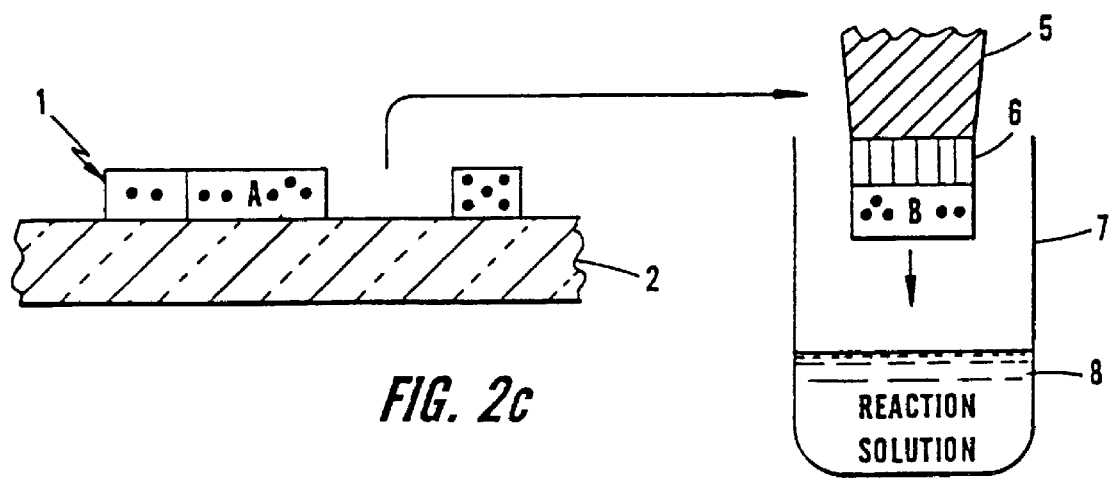

FIGS. 2a–2c are a series of functional system diagrams which show how a zone of tissue sample 1 is extracted from the slide-mounted tissue sample 1 according to one embodiment of the present invention. It is to be understood that the steps depicted in FIGS. 2a–2c could be either preformed manually by an operator or by a computer utilizing conventional positioning and control methods, e.g. computer controlled robotics.

The embodiment of the invention depicted in FIGS. 2a–2c utilize a contact probe 5 which has an adhesive/extraction reagent 6 on the tip thereof. A suitable adhesive/extraction reagent can include a mixture of piccolyte and xylene. In FIG. 2a the contact probe 5 is positioned either manually or by computer control so as to be above and aligned with the sample zone ("B") to be extracted. As can be readily understood from FIG. 2a, the surface area of the contact probe tip (and adhesive/extraction reagent) needs to be about equal to, and no greater than, the surface area of the zone to be extracted. Otherwise, excessive removal of adjacent tissue zones will occur.

Once the tip of the contact probe 5 is aligned with the sample zone ("B") to be extracted, the contact probe 5 is lowered so that the adhesive/extraction reagent 6 on the tip thereof contacts the sample zone (FIG. 2b).

The adhesive/extraction reagent 6 is selected to readily adhere to the sample zone. Once the adhesive/extraction reagent 6 on the tip of the contact probe 5 contacts the sample zone (FIG. 2b) and the sample zone becomes adhered thereto, the contact probe 5 can be retracted from the contact position (illustrated in FIG. 2b) and moved as shown in FIG. 2c. Since the relative adhesive force of the adhesive/extraction reagent is greater than the adhesive force used to mount the sample on the glass slide, the contact probe 5 pulls the sample zone "B" from the glass slide when withdrawn or retracted. According to one embodiment of the present invention, a glass pipette was used as the contact probe 5. In this embodiment, the tip of the glass pipette was coated with a solution of piccolyte (568 g/l) and xylene (437.5 g/l) by dipping the tip of the glass pipette in the piccolyte/xylene solution.

In addition to removing the sample zone from the glass slide 2, the contact probe 5 can be used to transfer the extracted sample zone to an analysis container 7 as indicated in FIG. 2c or to any other location, such as a waste container, a culture media, etc. In a preferred embodiment, the contract probe 5 is used to transfer the extracted sample zone to the sample receiving stage of an automated clinical analyzer which is designed to preform a desired analysis of the sample zone. It thus, can be understand that the present invention can provide a fully automated method and system for identifying sample zones on a slide-mounted sample, removing sample zones of interest from the slide-mounted sample, and transporting the extracted sample zones to an automated analyzer which can perform automated analysis of the extracted sample zones.

In FIG. 2c the extracted sample zone is depicted as being dispensed in a container 7 which, for example, can be a test tube or similar container in which analysis on the extracted sample zone can be initiated or performed. As depicted in FIG. 2c, a reagent solution 8 which removes all or a desired component of the extracted sample zone from the contact probe tip can be placed in the container 7 before the extracted sample zone is deposited therein. For example, in the case of DNA analysis, a solution of Tris (50 mM, pH8.5), EDTA (1 mM), Tween 20 (0.5%), and proteinase K (0.2 mg/mL) can be used to remove the extracted sample zone from the tip of the contact probe 5 and dissolve the tissue material for analysis purposes.

In addition to the contact probe depicted in FIGS. 2a–2c, a hollow suction probe could also be used to extract sample zones from the slide-mounted tissue sample 1. Such a suction probe could be provided with sharp annular tip by which sample zones could be punched out and extracted by suction forces.

Figure 3:
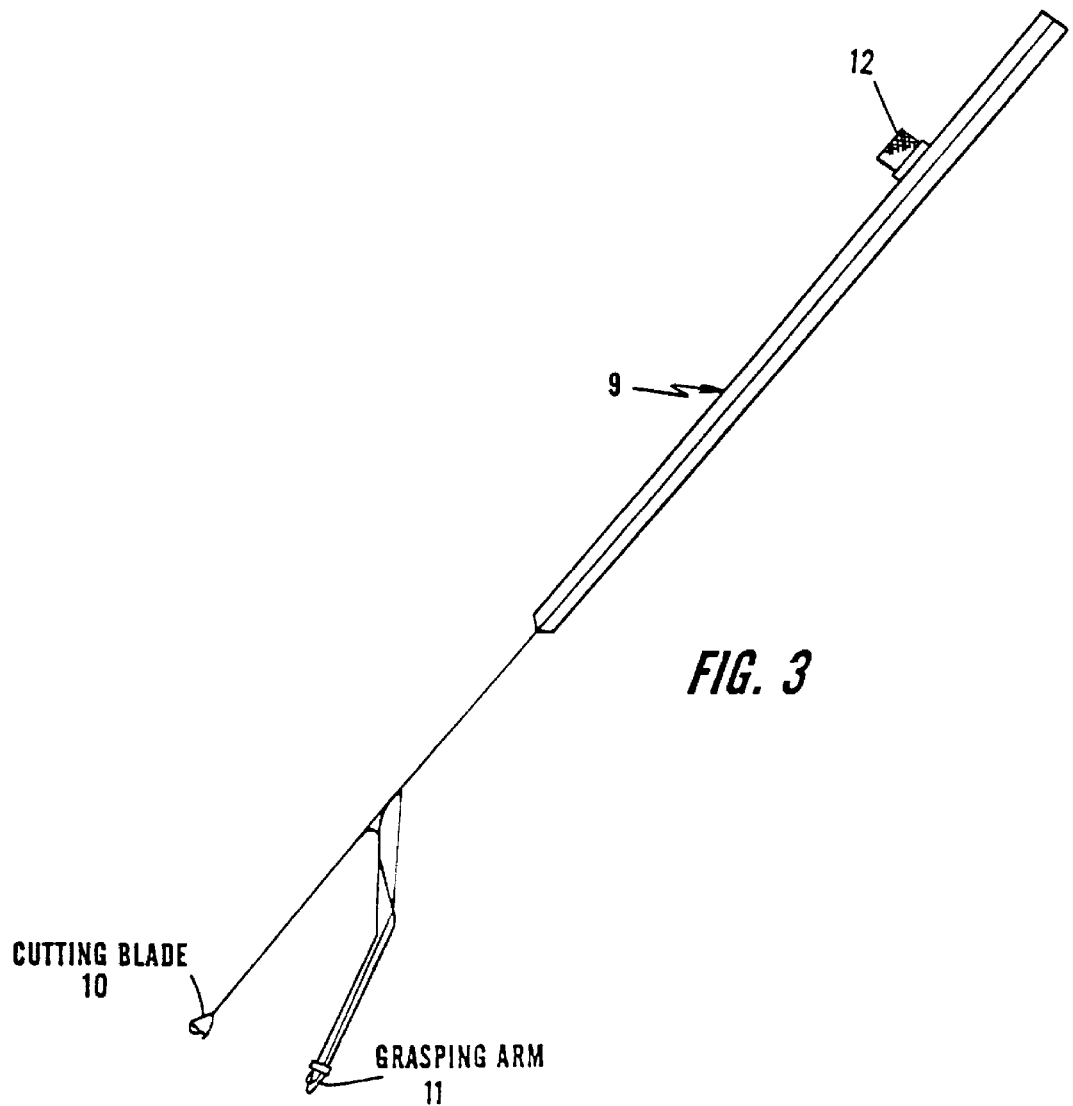
FIG. 3 is a schematic illustration of an alternative device for extracting sample zones from the slide-mounted tissue sample.

FIG. 3 is a schematic illustration of an alternative device for extracting sample zones from the slide-mounted tissue sample 1. The extraction device 9 shown in FIG. 3 includes a cutting blade 10 and a grasping arm 11. The grasping arm 11 can be moved in an opposed manner with respect to the cutting blade 10. The grasping arm 11 is shown in its open position in FIG. 3. The grasping arm 11 is movable between the illustrated open position to a closed position in which the tip of the grasping arm 11 contacts the cutting blade 10. The movement of the grasping arm 11 can be controlled by a cable and pulley system in which grasping arm 11 is caused to pivot at its base by applying tension to a cable which passes through a pulley located at the base of the grasping arm 11. The tension on the cable can be applied by actuating a lever or depressing a button 12 on the device which applied tension to the cable in a known manner. Such actuating mechanical structures are known in the art of gripping devices.

In operating the device of FIG. 3, the cutting blade 10, which is at an obtuse with respect to the central axis of the device can cut out and scoop up a portion of a tissue sample by placing the cutting blade 10 on one edge of a portion of the tissue sample to be extracted and then moving the grasping arm 11 into the closed position. As the grasping arm 11 comes into contact with the tissue sample, it draws the cutting blade 10 into the sample and presses a portion of the sample toward the cutting blade 10 thereby causing a portion of the sample contacted between the cutting blade 10 and the grasping arm 11 to be cut out and scooped up from the sample.

In a further, alternative embodiment of the device of FIG. 3, the movement of the grasping arm 11 can be effected by a toothed gear instead of a pulley and a cooperating toothed rod in place of a cable. Such mechanical structures are known in the art of gripping devices.

Figure 4B:
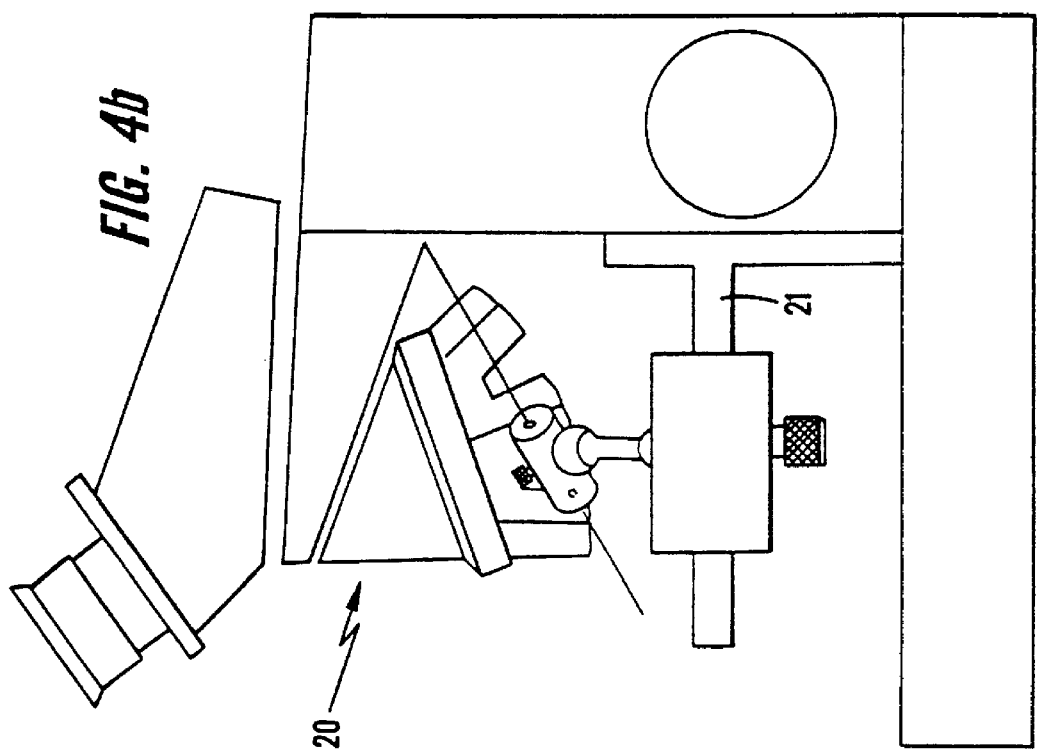
FIGS. 4a and 4b are schematic diagrams of a manual extraction tool manipulator which can be used together with the extraction device of FIG. 3 according to the present invention.
Figure 4A:
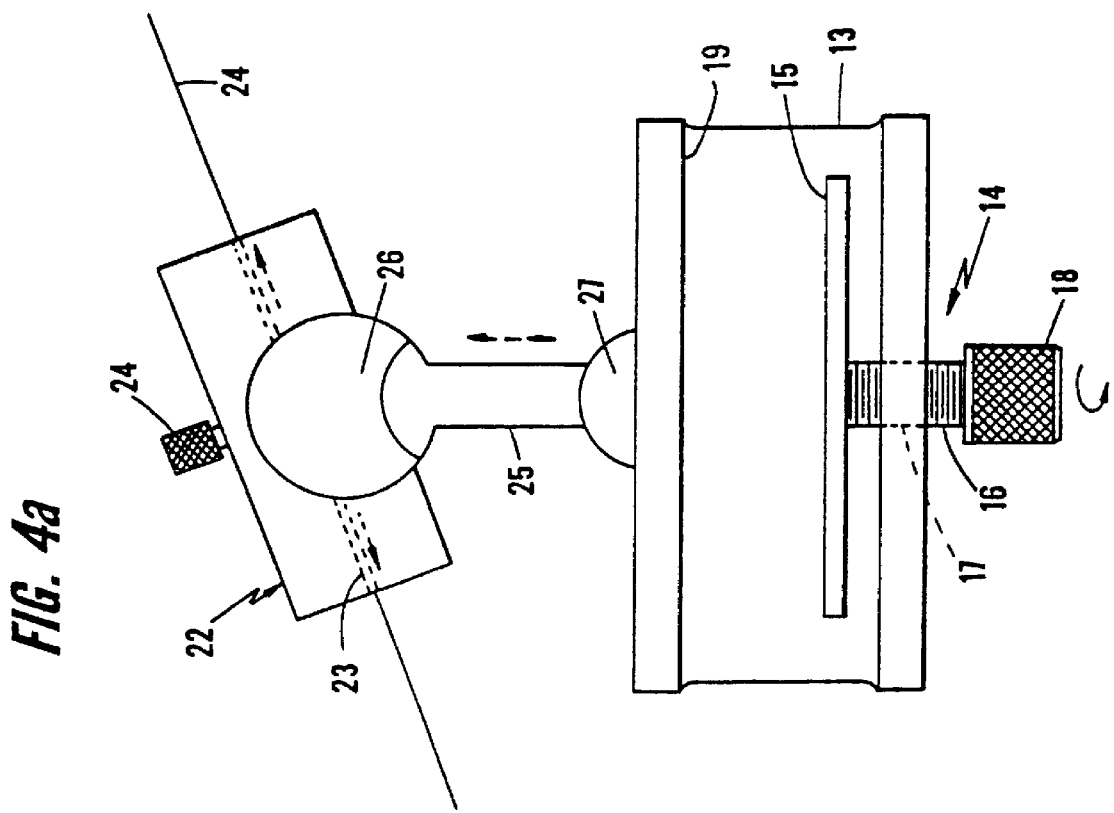

FIGS. 4a and 4b are schematic diagrams of a manual extraction tool manipulator which can be used together with the extraction device of FIG. 3 according to the present invention. In FIG. 4a the extraction tool manipulator is depicted as having a base 13 equipped with a clamping means 14 for removable attaching the device to a brace or support portion of the stage of a microscope (see FIG. 4b). The clamping mechanism includes a clamping plate 15 that is secured to a threaded shaft 16 which passes through a threaded bore 17 in a lower portion of the base 13. A tightening knob 18 is provided on the end of the threaded shaft 16. Turning the tightening knob 18 causes the clamping plate 15 to move with respect to an upper portion 19 of the base 13. Thus, the extraction tool manipulator can be clamped to a portion of the stage of a microscope 20 as depicted in FIG. 4b by positioning a brace or support portion 21 of the stage of the microscope 20 between the clamping plate 15 and the upper portion 19 of the base 13 and turning knob 18 to tighten the clamping plate 15 against the brace or support portion 21 of the stage of the microscope 20.

The extraction tool manipulator includes a tool holder 22 having a through-bore 23 therein for receiving the shaft of an extraction tool 24. Ideally, the tool holder 22 should allow for damped fore and aft movement of the extraction tool. Therefore, according to a preferred embodiments the through-bore 23 of the tool holder 22 contains a bushing which can be adjustable tightened against the tool shaft by tool locking screw 24.

The tool holder 22 is supported by support shaft 25 which is connected at opposite ends by 360° damped swivels 26 and 27 to the tool holder 22 and the base 13. The length of the support shaft 25 between the 360° damped swivels 26 and 27 is adjustable. The adjustment of the independent 360° damped swivels 26 and 27 together with the adjustable length of the support shaft 25 and the position of the tool shaft within through-bore 23, allows a high degree of movement of the extraction tool with respect to a slide-mounted sample positioned on the stage of the microscope. Therefore, an operator can manipulate an extraction tool held by the extraction tool manipulator and remove selected tissue zones from a slide-mounted tissue sample with a high degree of precision.

FIG. 5 is a functional system diagram which shows how a zone of sample tissue can be directed to an appropriate analysis protocol. As depicted in FIG. 5 a microextraction of a zone of tissue sample can be taken from a slide-mounted tissue sample 1 as discussed above and transferred to a sample preparation stage 28 in which the cells of interest can be extracted and collected for analysis. Excised cells may also be solubilized at this stage. If the cells of interest contain DNA or RNA the extracted sample is subjected to polymerase chain reaction (PCR) amplification and hybridization, strand conformational polymorphism, and southern and northern blotting as desired. If the cells of interest contain proteins, the extracted sample can be subjected to enzyme zymography, an immunoassay, or a biochemical assay.

Selective extraction or microdissection of frozen tissue sections according to the present invention allows for recovery and analysis of both active enzymes and MRNA. Additionally, the DNA recovered from these sections is in the native condition and can be used for studies such as DNA fingerprinting. Microdissection of paraffin embedded tissues according to the present invention allows for PCR amplification of DNA from pure cell populations representing less than one high powered field, or a single layer of epithelial cells lining cystic spaces.

For general preparation of samples for frozen section microdissection according to the present invention microdissection slides can be prepared by placing 1% agarose on a standard histology slide and cover slipping. After a short period of time, e.g., 5 minutes the cover slip is removed leaving a thin gel on the slide. A small frozen tissue section, e.g. 25 micron thick, is placed on the agarose gel and briefly stained with eosin. The tissue may also be treated with agents to denature RNase depending on the subsequent extraction method. Under direct microscopic visualization the specific cell population or sub-population of interest is procured from the tissue section utilizing the techniques discussed above.

For enzyme analysis the procured tissue specimen can be placed in an appropriate buffer depending on the enzyme of interest. The enzyme levels can be measured by several methods including zymography and the use of specific fluorometric substrates. The precise levels of enzyme expression in a specific cell population can be determined.

For messenger RNA analysis the tissue specimen can be placed on agarose and treated with agents to denature RNase if necessary. The procured tissue specimen is immediately frozen in liquid nitrogen. The tissue can be used immediately or stored at −70° C. for several months. The MRNA can be extracted using an oligo dT column (Micro-Fast track MRNA Isolation Kit, Invetrogen Co.). The recovered MRNA of the pure cell populations can be amplified and investigated using PCR technology.

For DNA analysis the tissue specimen can be placed in a single step extraction buffer solution of 50 mM Tris, pH 8.5; 1 mM EDTA, 0.5% Tween 20, and 0.2 mg/ml proteinase K, incubated for four hours at 37° C., followed by ten minutes incubation at 95° C. The recovered DNA can be amplified and analyzed by PCR technology. If native DNA is required for DNA fingerprinting, the proteinase K can be added after DNase.

For paraffin section microdissection routine formalin fixed, paraffin embedded tissue sections are microdissected after deparaffinization and brief staining with eosin. Tissue sections are visualized by direct microscopy and cell populations or subpopulations of interest are procured using a modified glass pipette with the adhesive coated tip discussed above. Tissue specimens as small as one cell can be procured with this method. The specificity of dissection represents a significant improvement over currently known techniques.

For DNA analysis of paraffin embedded tissue, the glass pipette with the dissected tissue specimen is placed in a single step extraction buffer solution of 50 mM Tris, pH 8.5; 1 mM EDTA, 0.5% Tween 20, and 0.2 mg/ml proteinase K which removes the tissue from the pipette tip. Depending on the size of the sample it is incubated from two to twenty-four hours at 37° C., followed by a ten minute incubation at 95° C. The glass pipette tip can then be sterilized and reused.

Features and characteristics of the present invention will be illustrated by the following examples to which the present invention is not to be considered limited. In the examples and throughout percentages are by weight unless otherwise indicated.

The following examples were performed in an attempt to establish if the present invention could be used to more specifically study protease distribution during human tumor invasion. Levels of MMP-2 and cathepsin B in fields of invasive breast and colon carcinoma were measured to assess if the enzymes in these regions were quantitatively increased as compared to matched numbers of normal cells from the same patient.

In the following examples, normal and tumor samples of colon and breast tissue from surgical resections were maintained in a frozen condition (−70° C.) until analysis. Tissue section of invasive breast and colon carcinoma were selected based upon histologic evaluation. For the tumor sections histologic fields of tissue which contained invasive tumor and stroma were selected, but not normal epithelium or significant numbers of inflammatory cells. The control sections of normal tissue contained epithelium and a thin section of underlying stroma. The proportion of epithelial and stromal tissue was similar for both normal and tumor sections.

In the examples microdissection slides were prepared by covering standard histology slides with 200 microliters of warm agarose (1%) and over laying a cover slip. After five minutes the coverslip was removed leaving a thin bed of agarose on the slide. Twenty micron thick frozen sections were prepared in a cryostat and placed on the agarose gel. The tissue was briefly dipped in eosin. Optimum microdissection was achieved by starting at the edge of each section and systematically dissecting and separating histologic fields of interest with the microdissecting device of FIG. 3. Areas of interest were retained on the slide for subsequent analysis. The DNA content of the specimens was determined by spectrophotometric measurement at 260 nm. The DNA content of each sample was proportional to the number of cells counted in each histologic section.

EXAMPLE 1

In this example, samples of normal and tumor tissue matched for cell number were analyzed from each subject. Levels of MMP-2 were determined by zymography and quantified using an Arcus scanner. Results were statistically analyzed using the students t-test. Cathepsin B levels were determined as $V_{max}$ against the substrate Z-Arg-Arg-NHMec.

The results of this example are set forth in Table 1 below which lists the cathepsin B activity in matched pairs of invasive colon carcinoma/normal epithelium, and invasive breast carcinoma/normal epithelium. Activity measurement are expressed as $V_{max}$, nmol/min×mg DNA. Cathepsin B activity was increased an average of 2.3 fold in the colon tumors (p<0.005), and 6.9 fold in the breast tumors (p=0.077).

TABLE 1

| SAMPLE | NORMAL | TUMOR | TUMOR/NORMAL |
|---|---|---|---|
| CATHEPSIN B ACTIVITY IN INVASIVE HUMAN COLON CARCINOMA | | | |
| 1 | 1.38 | 4.75 | 3.4 |
| 2 | 1.89 | 2.25 | 1.2 |
| 3 | 1.98 | 6.32 | 3.2 |
| 4 | 0.49 | 1.88 | 3.8 |
| 5 | 0.44 | 0.72 | 1.6 |
| 6 | 1.03 | 1.92 | 1.9 |
| 7 | 0.47 | 1.35 | 2.9 |
| 8 | 0.19 | 0.33 | 1.7 |
| 9 | 1.07 | 0.90 | 0.8 |
| 10 | 0.33 | 0.88 | 2.7 |
| Average | 0.93 | 2.13 | 2.3 |
| CATHEPSIN B ACTIVITY IN INVASIVE HUMAN BREAST CARCINOMA | | | |
| 1 | 0.63 | 3.02 | 4.8 |
| 2 | 0.51 | 10.08 | 19.8 |
| 3 | 0.61 | 4.43 | 7.3 |
| 4 | 2.21 | 2.38 | 1.1 |
| 5 | 2.06 | 3.72 | 1.8 |
| Average | 1.20 | 4.73 | 6.9 |

As can be seen from Table 1, all five breast tumors and nine of the ten colon tumors showed increased activity of cathepsin B as compared to matched numbers of normal cells from the same patient (Table 1). Increased activity in the colon tumors ranged from 19% to 283%, with an average increase in tumors of greater than two fold. The increase of cathepsin B activity was more pronounced in breast tumors with an average increase of slightly less than seven fold.

EXAMPLE 2

In this example, polymerase chain reaction (PCR) analysis was preformed. On the basis of previously reported CDNA sequences of 72 kDa type IV collagenase, sense and antisense oligonucleotide primers were synthesized for amplification of the enzyme activation site (M. Onisto et al, "Reverse Transcription-Polymerase Chain Reaction Phenotyping of Metalloproteinases and Inhibitors in Tumor Matrix Invasion", *Diagn. Mol. Pathol*, 2(2):74–80, 1993). The paired oligonucleotide sequences were: 5'-CAA TAC CTG AAC ACC TTC TA, 3'-CTG TAT GTG ATC TGG TTC TTG. Labeled PCR for Single Strand Conformation Polymorphism (SSCP) was obtained by combining the following in a 10 microliter reaction: 1 microliter 10× PCR buffer (100 mM Tris-HCL, pH 8.3; 500 mM KCl; 15 mM $MgCl_2$; 0.01% w/v gelatin); 1 microliter of DNA extraction buffer; 50 pmol of each primer; 20 nmol each of dCTP, dGTP, dTTT, and dATP; 0.2 microliter [$^{32}$P]dCTP (6000 Ci/mmol); and 0.1 unit Taq DNA polymerase. The amplification reaction was carried out for 30 cycles at 95° C. for 30 s, 60° C. for 30 s, and 72° C. for 30 s.

Figure 6A:
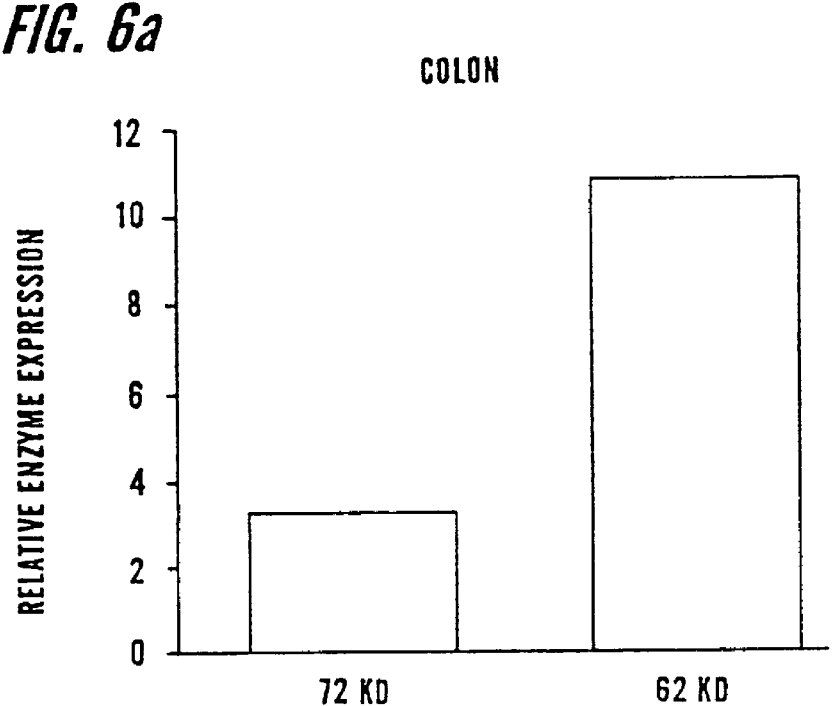
FIGS. 6a and 6b show the expression of MMP-2 in ten invasive colon carcinoma cases (FIG. 6a) and in five cases of invasive breast carcinoma (FIG. 6b) as compared to normal colonic mucosa from the same patients.

FIG. 6a shows the expression of MMP-2 in ten invasive colon carcinoma cases as compared to normal colonic mucosa from the same patients. The bar graphs show increases of approximately three fold in the 72 kDa pro-form of the enzyme (p<0.001) and ten fold in the 62 kDa active form of the enzyme (p<0.001).

Figure 6B:
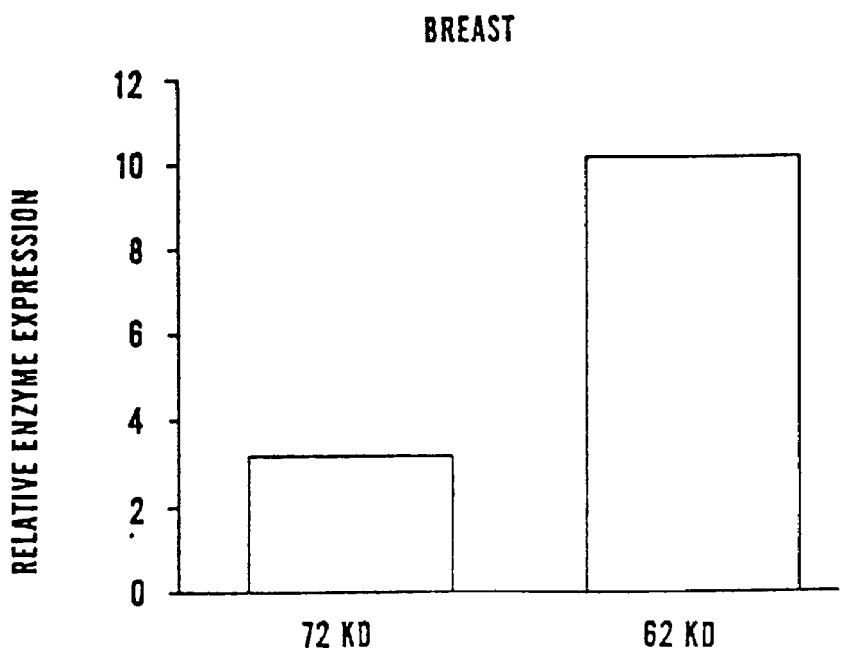

FIG. 6b shows the expression of MMP-2 in five cases of invasive breast carcinoma. The bar graphs show an appropriate increase of three fold in the 72 kDa proform of the enzyme (p<0.05) and ten fold in the 62 kDa active form of the enzyme (p<0.05).

The 72 kDa pro-type IV collagenase and 62 kDa active form of the enzyme were increased in all ten colon tumors and all five breast tumors as compared to normal tissue from the same patient. The increase was greater in the 62 kDa active form of the enzyme which was elevated an average of ten-fold in both the colon and breast tumors as compared to normal control tissue. The 72 kDa pro-enzyme levels were increased an average of three fold in both tumor types. For both breast and colon tumors the increase in the 62 kDa active enzyme was more variable than that of the pro-enzyme. Elevations in the 62 kDa active enzyme in tumors ranged from 3 to 20 fold while increases in the 72 kDa pro-enzyme were consistently in the 2 to 5 fold range. These results are similar to the recent findings of Davis et al ("Activity of Type IV Collagenases in Benign and Malignant Breast Disease", *Br. J. Cancer*, 67:1126–1131, 1993) in their analysis of human breast tumors. These authors performed zymogram analysis of tissue sections from human breast cancer patients. These analyses demonstrated that the fraction of total MMP-2 present as the 62 kDa activated form was statistically elevated in malignant disease, and a high proportion of this active enzyme species was detected in higher grade tumors. The present invention extends this analysis by comparing and quantitating both 72 kDa and 62 kDa forms of the enzyme in specific regions of invasive tumor and matched normal control epithelium from the same patient.

EXAMPLE 3

In this example, strand conformation polymorphism (SSCP) analysis was preformed. Labeled amplified DNA was mixed with an equal volume of formamide loading dye (95% formamide; 20 mM EDTA; 0.05% bromophenol blue, and 0.05% xylene cyanol). The samples were denatured for 5 min at 95° C. and loaded onto a gel consisting of 6% acrylamide (49:1 acrylamide:bis), 5% glycerol, and 0.6× TBE. Samples were electrophoresed at 8 W at room temperature overnight. Gels were transferred to 3 mm Whatman paper, dried and autoradiography was performed with Kodak X-OMAT film.

Figure 7:
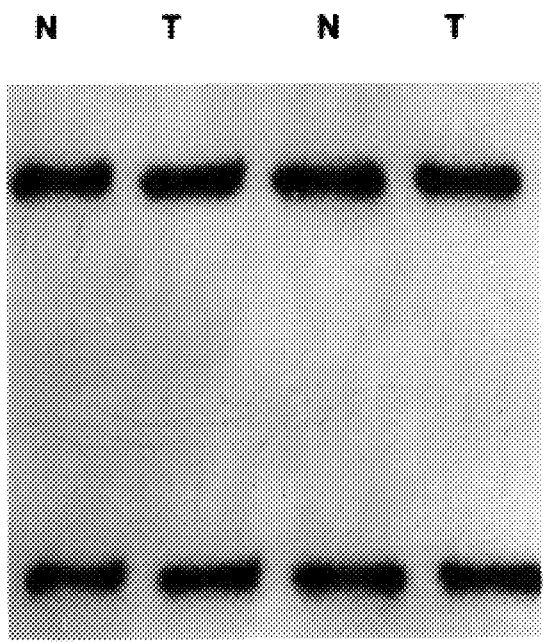
FIG. 7 shows SSCP analysis of MMP-2 activation site.

FIG. 7 shows SSCP analysis of MMP-2 activation site. The figure shows representative cases of normal colon is mucosa compared to invasive colon carcinoma, and normal breast tissue compared to invasive breast carcinoma. No difference is observed between the normal and tumor specimens. The two band in each lane represent single and double forms of DNA. Similar results were obtained for ten colon carcinomas and four breast carcinomas.

To assess if increased tumor levels of activated MMP-2 are due to a mutation in the enzyme, PCR was used to amplify DNA sequence coding for the activation site of gelatinase A from the colon and breast tumors. The activation site is located 10 kDa from the N-terminus of the enzyme and contains the site of cleavage which converts the 72 kDa pro-enzyme into the 62 kDa active species. Amplification and analysis of this region by PCR and SSCP showed no detectable mutations in any of the ten colon tumors or four breast tumors studied. These results suggest that increased levels of active enzyme in invasive tumors is most likely due to a tumor associated activating species. The sensitivity of PCR amplification of DNA from microdissected frozen tissue sections was determined to be less that one high power field. Similar to the amplification of DNA, amplification of mRNA from small cell populations was preformed according to the present invention using reverse PCR.

A previous study indicated that MMP-2 is upregulated in human colon carcinoma. However, recently several studies using in situ hybridization analysis report that the MRNA level of MMP-2 in human colon carcinoma is increased in the stromal cells as opposed to the tumor cells. In order to address this possibility frozen tissue sections were microdissected to measure enzyme levels of MMP-2 in separate tumor and stromal cell populations. From a single high power field sufficient tissue was recovered to quantitate enzyme levels by zymography. Studies of invasive tumor cells and adjacent stroma from three cases indicate that 72 kDa pro-MMP-2 and active 62 kDa form are associated with both tumor cell and stromal cell populations. Preliminary data suggest that the highest enzyme levels are at the tumor-stromal interface.

According to a preferred embodiment, the present invention is directed to adhesive transfer methods which involve microscopic visualization and transfer of cellular material to a procurement or transfer surface.

According to the general procedure, an adhesive surface is placed in contact with the surface of the cells or tissue and the adhesive force binds the cellular material of :interest to the adhesive surface. The adhesive surface which can be the tip of a tool or needle is used to procure the material and transfer it to a liquid analysis reaction mixture. Examples of adhesive surfaces include adhesive coatings on the tip of the tool, or the use of electrostatic forces between the tip and the surface of the cellular material.

As described in detail below, the isolation and transfer methods of the present invention can involve a specialized continuous activatable adhesive layer or surface which is applied to the cellular material over an area larger than the area selected for microscopic procurement. The adhesive function of the subsection of the surface in contact with the area selected for procurement is activated by electromagnetic or radiation means. According to a preferred embodiment a laser or other electromagnetic radiation source is used to activate the adhesive forces between the cellular material and the activatable adhesive layer or surface. This allows for accurate generation of adhesive forces only in the precise microscopic area selected. Suitable lasers include diode-pumped Nd, YAG and Nd:Yag, tunable single frequency Ti:sapphire lasers, solid state lasers. Lasers having wavelength outputs from ultraviolet to infrared can be used according to the present invention.

In addition to lasers, it is possible to activate adhesive layer utilizing electrically heated radiation heaters or heated probes, focused or masked non-laser light sources such as flashbulbs, xenon lamps, etc.

FIGS. 8a–8d are schematic illustrations of the sequential steps of an adhesive transfer method according to one embodiment of the present invention.

Figure 8A:
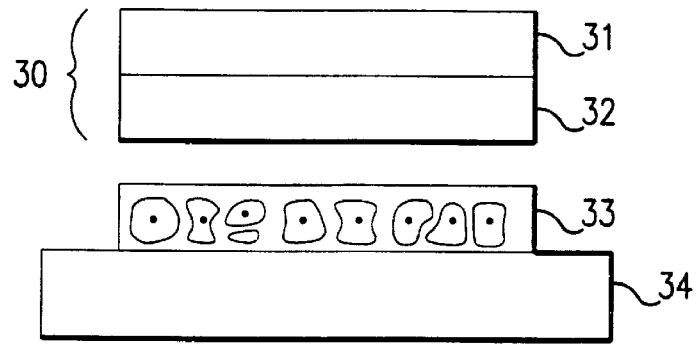
FIGS. 8a–8d are schematic illustrations of the sequential steps of an adhesive transfer method according to one embodiment of the present invention.

As depicted in FIG. 8a, the adhesive transfer method utilizes a transfer surface 30 which includes a backing layer 31 and an activatable adhesive layer 32. In procedures which utilize laser activation of the adhesive layer, the backing layer 31 is preferably transparent, e.g. made of a transparent polymer, glass, or similar material. The activatable adhesive layer 32 can be an emulsion layer, a coated film, or a separate impregnated web fixed to the backing layer. Examples of materials from which the adhesive layer 32 can be make include thermal sensitive adhesives and waxes (e.g., #HAL-2 180C from Precision Coatings), hot glues and sealants (available from Bay Fastening Systems, Brooklyn, N.Y.), ultraviolet sensitive or curing optical adhesives (e.g., N060-N0A81, ThorLabs Inc.), and thermal or optical emulsions (e.g., silkscreen coated emulsion B6 Hi Mesh, Riso Kagaku Corp.)

The backing layer 31 provides physical support for the adhesive surface, and thus can be integrated physically into the activatable adhesive surface.

The activatable adhesive layer 32 is characterized by its ability to be stimulated (activated) by electromagnetic radiation so as to become locally adherent to the tissue. For purposes of selectively activating the activatable adhesive layer 32 one or more chemical components can incorporated into the layer, which chemical components cause selective absorbance of electromagnetic energy.

As depicted in FIG. 8a, the transfer surface 30 is initially positioned over a cellular material sample 33 which can be a microtome section or cell smear which is supported on a support member 34 which can be a microscopic slide. In the case of a tissue microtome, routine procedures can be used to provide paraffin embedded, formalin-fixed tissue samples.

Figure 8B:
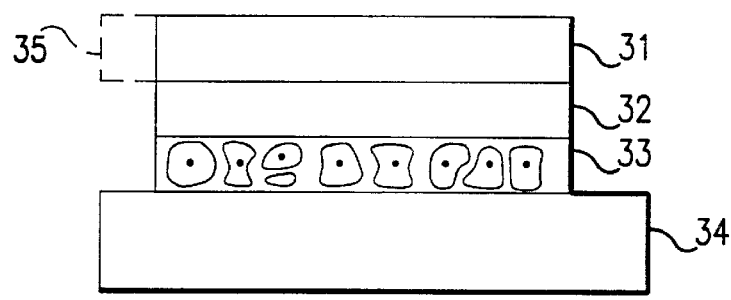

As shown in FIG. 8b, the transfer surface 30 is brought into contact with the cellular material sample 33. It is noted that the activatable adhesive layer 32 preferably has a larger area than the subregion of cellular material sample which is subsequently selected for procurement.

The transfer surface 30 can be fixed to the cellular material sample support 33 by clips, guides, tape, standard adhesives, or similar convenient means. The transfer surface 30 can also contain a label region 35 (see phantom lines in FIG. 8b) to write information such as the patient's identification code or a test designation.

Figure 8C:
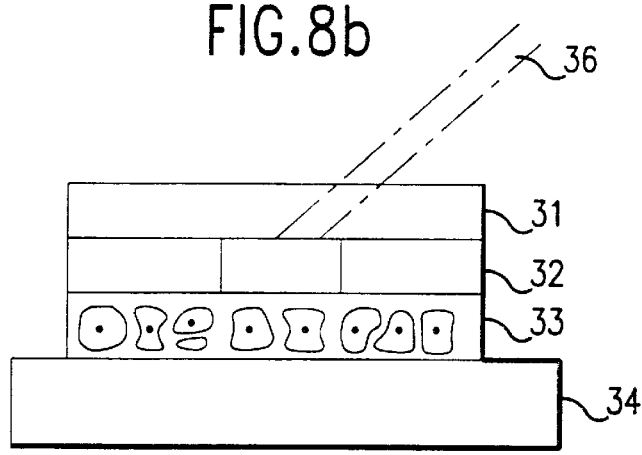

After the transfer surface 30 is brought into contact with the cellular material sample 33, the cellular material sample is viewed by standard low or high power microscopy to locate the region of interest "A". This region can range in size to an area smaller than a single cell (less than 10 microns), to a few cells, to a whole field of cells or tissue. When the area of interest "A" is identified, the precise region of the activatable adhesive layer 32 which is immediately above region "A" is activated by a beam of electromagnetic energy 36, e.g. a laser beam, as depicted in FIG. 8c.

Application of the electromagnetic energy 36 causes the region of the activatable adhesive layer 32 which is immediately above region "A" to adhere to region "A". Although FIGS. 8c and 8d depict a single region of interest "A", it is to be understood that multiple, discontinuous regions of interest could be selected and procured by appropriate aiming and application of the electromagnetic energy.

Figure 8D:
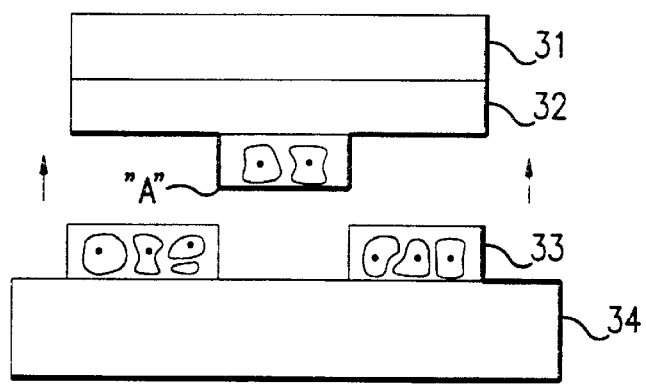

As depicted in FIG. 8d, after one or more regions of interest are identified and the corresponding region(s) of the activatable adhesive layer 32 is activated by a beam of electromagnetic energy 36, the transfer surface 30 is detached from the cellular material sample support 34. As shown, the removed transfer surface 30 carries with it only the precise cellular material from the region of interest "A", which is pulled away from the remaining cellular material sample.

As mentioned above, a single transfer surface can be used to remove a plurality of areas of interest from a single cellular material sample. The transfer surface 30 carrying the procured cellular material can be treated with suitable reagents to analyze the constituents of the transferred material. This can be accomplished by submerging the transfer surface 30, to which the procured cellular material is adhered, in a suitable reagent solution. Alternatively, one or more of the procured cellular material regions can be removed from the transfer surface 30, or portions of the transfer surface 30 to which the procured cellular material are adhered can be punched out of the transfer surface 30 and analyzed separately.

In the following Examples 4 and 5, the following sample procurement method was followed. 5–10 micron sections of formalin-fixed, paraffin-embedded tissue or froze tissue were prepared on a glass slide according to conventional surgical pathology protocol. The paraffin sections were deparaffinized with xylene (x2), 95% ethanol (x2), 50% ethanol (x2), distilled water (x2), and air dried. Frozen or paraffin sections were stained briefly in eosin (1% eosin in 80% ethanol) and air dried.

An adjacent hematoxylin and eosin section was used to assess the tissue section for optimal areas of microdissection, i.e., localization of specific small cell populations of interest, exclusion of regions which contain significant inflammation, etc.

Microdissection of selected populations of cells was performed under direct light microscope visualization. A sterile 30 gage needle was used as the transfer surface. Electrostatic interaction between the needle and cellular material provided the adherence needed to remove selected populations of cells. It was determined that pure cell populations of as little as 5 cells could be procured. In addition it was found possible to procure cells arranged as a single cell layer, i.e., normal epithelium, epithelial lining of cystic lesions, etc.

EXAMPLE 4

Human prostate cancer has been proposed to progress through an in situ tumor phase called prostatic intraepithelial neoplasia (PIN) prior to evolving into overtly invasive cancer. PIN lesions are frequently found in association with prostate carcinoma, and histologically the cells in PION foci have several features similar to those of invasive prostate cancer cells. Previous reports have shown that PIN lesions are frequently aneuploid. However the precise relationship between PIN and invasive carcinoma has remained unclear.

In this Example, frozen normal and tumor prostate samples from 100 patients treated with transurethral prostatectomy or radial prostatomy were collected. Of these, 30 cases which contained clearly invasive cancer as well as at least one focus of identifiable PIN were selected for study during this Example. Fourteen of the set cases contained more than one focus of PIN. The histopathology of the tumors was variable and included well differentiated, moderately differentiated and poorly differentiated. PIN lesions were both low and high grade.

Microdissection of selected populations of normal epithelial cells, cells from PIN lesions, and invasive tumor cells from frozen tissue sections was performed under direct light microscopic visualization utilizing the method discussed above. Specific cells of interest were microdissected and procured from unstained 8 μm frozen sections. In each case, normal epithelium, PIN cells, and invasive tumor cells from the same patient were analyzed.

Procured: cells were immediately resuspended in a 20 ml solution containing 10 mM Tris-HCL, pH 8.0, 100 mM ethylenediamine tetraacetic acid (EDTA), 1% Tween 20, 0.1 mg/ml proteinase K, and incubated overnight at 37° C. The mixture was boiled for 5 minutes to inactivate the proteinase K and 0.5–2% of this solution was used for polymerase chain reaction (PCR) analysis.

The oligonucleotide primers D8S136, D8S137, and NEFL were used to locate chromosome 8p12-21. Reactions with D8S137 and NEFL were performed in an MJ Research thermal cycler as follows: 2 minutes at 950° C., followed by 40 cycles of: 950° C. for 30 seconds, 620° C. for 30 seconds, 720° C. for 30 seconds, followed by a final 2 minute incubation at 720° C.

Reactions with D8S136 were cycled as follows: 2 minutes at 950° C., followed by 40 cycles of: 950° C. for 30 seconds, 550° C. for 30 seconds, 720° C. for 30 seconds, followed by a final 2 minute incubation at 720° C.

PCR was performed in 12.5 ml reactions with 200 mM dNTP, 0.8 mM primers, 2 μl of alpha [$^{32}$P]dCTP (NEN), and 1 unit of Taq polymerase. Labeled amplified DNA was mixed with an equal volume of formamide loading dye (95% formamide; 20 mM EDTA; 0.05% bromophenol blue, and 0.05 xylene cyanol).

The samples were denatured for 5 min at 950° C. and loaded into a gel consisting of 7% acrylamide (49:1 acrylamide:bis), 5.7M urea, 32% formamide, and 0.089M Tris, 0.089M borate. 0.002M EDTA (1×TBE). Samples were electrophoresed at 95 Watts for 2–4 hours. Gels were transferred to 3 mM Whatman paper, and autoradiography was performed with Kodak X-OMAT film. The criterion for LOH was complete, or near complete absence of one allele as determined by visualization. Cases with LOH showed two alleles in the normal epithelium control and one allele in the tumor or PIN all with similar intensities. Cases with complete or near complete loss (i.e., very faint band) of one allele in tumor or PIN were considered positive for LOH at that marker.

The present inventive method was used to microdissect cells from tissue sections to study loss of heterozygosity on chromosome 8p12-21 in patients with both prostatic carcinoma and adjacent foci of PIN. Tissue microdissection was conducted on 30 patients with concomitant PIN and invasive prostate cancer. In each case normal epithelium, invasive prostate cancer and at least one focus of PIN from the same patient were examined. In 14 cases multiple foci of PIN were examined. In all cases each individual PIN lesion and corresponding invasive tumor were selectively microdissected from of adjacent stroma, normal epithelium and inflammatory cells. Essentially pure populations of cells of interest were procured.

LOH on chromosome 8p12-21 occurred in at least one PIN lesion in 26 of 29 (89.6%) informative cases. Fourteen of the cases contained more than one PIN lesion. Eleven of these cases showed different allele loss patterns among the PIN lesions, including loss of opposite alleles. In total, 8p12-21 LOH was seen in 63.6% (35/55) of PION lesions studied. Allelic loss of chromosome 8p12-21 was seen in invasive tumors in 28 of 29 (96.5%) patients. In contrast with the success associated with the adhesive transfer technique of the present invention, the use of a scraping dissection technique produced an LOH of less than 15%. This indicates the sensitivity of the adhesive transfer of the present invention is much greater than conventional techniques.

EXAMPLE 5

Nascent in situ breast carcinomas are frequently observed arising in association with a spectrum of epithelial hyperplasias and invasive carcinoma. Pathologists have historically interpreted the common association of atypical hyperplasia, in situ carcinoma and invasive carcinomas as evidence for a relationship among the entities.

The polymorphic DNA marker used in this Examiner was PYGM located on chromosome 11q13. Reactions were cycled in a thermal cycler as follows: 94° C. for 1.5 min., 55° C. for 1 min., 72° C. for 1 min. for a total of 35 cycles. PCR was performed in 10 $\mu$l volumes and contained 1 $\mu$l 10×PCR buffer (100 mM Tris-HCl, pH 8.3; 500 mM KCl; 15 mM $MgCl_2$; 0.1% w/v gelatin; 2 $\mu$l of DNA extraction buffer, 50 pM of each primer; 20 nM each of dCTP, dGTP, dTTP, and dATP; 0.2 $\mu$l [$^{32}$P]dCTP (6000 Cl/mM); and 0.1 unit Taq DNA polymerase. Labeled amplified DNA was mixed with an equal volume of formamide loading dye (95% formamide; 20 mM EDTA; 0.05% bromophenol blue; and 0.05% xylene cyanol). The samples were denatured for 5 min. at 95° C. and loaded into a gel consisting of 6% acrylamide (49:1 acrylamide:bis). Samples were electrophoresed ar 1800 volts for 2–4 hours. Gels were transferred to 3 mM Whatman paper, dried and autoradiography was performed with Kodak X-OMAT film. The criterion for LOH from the microdissected in situ and invasive breast samples was complete absent of an allele.

Using the adhesive transfer technique of the present invention, cells were microdissected from normal epithelium, in situ carcinoma and invasive carcinoma from 8 $\mu$m thick formalin fixed deparaffinized sections from individual biopsies. Allelic loss of chromosome 11q13 was found in 69% of human breast carcinoma cases studied (n=105). The allelic loss was observed in both the in situ and invasive components of the tumors. In all cases (26/28) where in situ and invasive cancer was present in the same section, the identical allele was lost in the in situ and the invasive carcinoma. This provides molecular support for the long held hypothesis that in situ breast cancer is a precursor to invasive cancer.

In order to finely map the LOH locus on chromosome 11q13, Genome center provided a series of SSCP probes mapped to the relevant region of chromosome 11. The initial LOH area was determined to be bracketed by the proximal marker PYGM, and by the distal marker INT-2. A subset of 20 of the 105 cases exhibited LOH of either INT-2 or PYGM, but not both. Using these special cases, a series of intervening markers were used to map the smallest overlapping region between INT-2 and PYGM which shows LOH. It has been possible to pinpoint the LOH zone to a region encompassed by only one or two YAG or Cosmid clones at a location which overlaps with the MEN-1 (Multiple Endocrine Neoplasia type 1) locus.

Figure 9:
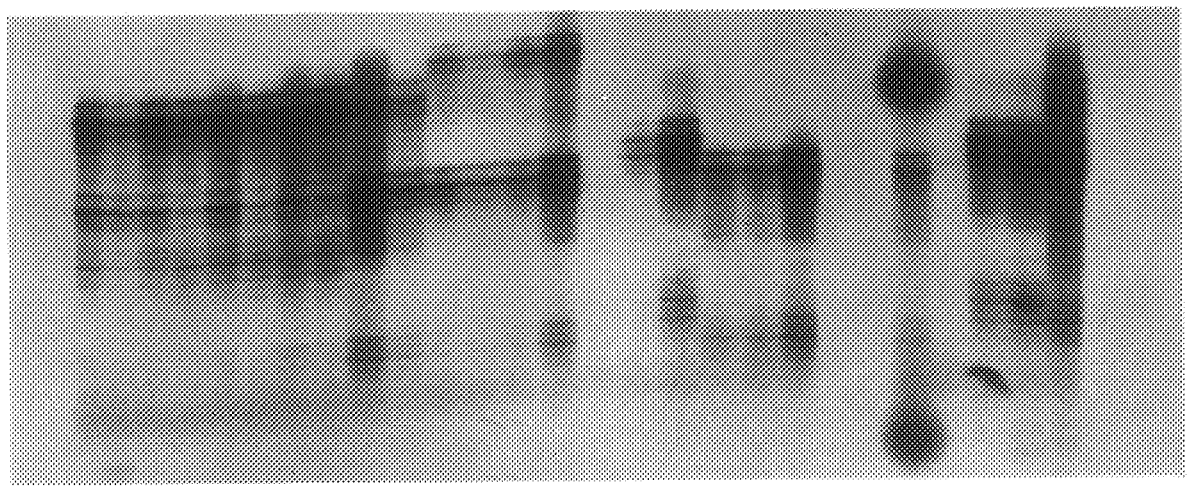
FIG. 9 shows the results of a sequencing gel electrophoresis of PCR amplified DNA from human tissue microdissected by the method depicted in FIGS. 8a–8b.

FIG. 9 shows the results of a sequencing gel electrophoresis of PCR amplified DNA from human tissue microdissected by the method depicted in FIGS. 8a–8d. Each numbered lane in FIG. 9 is from an individual dissection. Electrostatic transfer is shown in lanes 17–20. Lanes 18–20 show complete loss (positive LOH) of the top allele compared to the microdissected control DNA in lane 17. Thermal infrared transfer (conducted as shown in FIGS. 8c and 8d) is shown in lanes 22–25. Lane 22 (control) shows no DNA transfer without activation. Lanes 23 and 24 show complete loss (positive LOH) of top allele group compared to control DNA lane 25.

The above results indicate that microdissection of frozen tissue sections allows for more specific analysis of cell populations within human tumors than by conventional techniques. The microdissection technique of the present invention may be used in combination with a number of different technologies that allow for analysis of enzymes, MRNA and DNA from pure populations or subpopulations of particular cell types. For example, DNA can be microdissected, using the techniques of the present invention, from normal epithelium, pre-malignant lesions, and invasive cancer in the same patient's single tissue sections. This RNA can then be used to generate differential gene expression libraries by standard RT PCT. These libraries represent cellular stages of cancer progression. As such, they can be used to screen for cancer diagnostic and prognostic markers.

This simple technique may have utility in characterizing protease distribution during human tumor invasion, precisely determining protease expression in tumor and/or stromal cell populations as an indicator of tumor aggressiveness, and monitoring the effectiveness of anti-protease therapeutic agents in inhibiting protease activity at the tumor-stromal interface. In addition, combination of this microdissection technique with PCR, RT PCR, differential display and SSCP may identify genetic alterations in specific subpopulations of tumor or stromal cell that would not be evident in heterogeneous human tumor samples.

The present invention has applications in routine diagnosis of human tumors including microdissection of pre-malignant lesions of all types of cancer, genetic analysis of infectious diseases, gene therapy, tissue transformation, and gene localization and analysis of transgenic animals. Additional applications of this technique include analysis of the genotype, cellular products, or infesting organisms of rare populations such as Monocytes infected with drug resistant organisms, Reed-Stemberg cells of Hodgkins disease, Kaposi's sarcoma cells, stem cells, and vessel cells. Moreover, genetic analysis, or identification of, micro-organisms infesting microscopically visualized cells in tissues, lymph nodes or inflammatory areas can also be accomplished with high precision Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

We claim:

1. A method of direct extraction of cellular material from a tissue sample which comprises:

provideing a tissue sample;

contacting said tissue sample with a selectively activatable transfer surface which can be activated to provide selective regions thereof with adhesive characteristics;

identifying at least one portion of said tissue sample which is to be extracted;

selectively activating a region of said transfer surface which corresponds to and is in contact with said at least one portion of said tissue sample so that said activated region of said transfer surface adheres to said at least one portion of said tissue sample; and separating said transfer surface from said tissue sample while maintaining adhesion between said activated region of said transfer surface and said at least one portion of said tissue sample so that said at least one portion of said tissue sample is extracted from a remaining portion of said tissue sample.

2. A method of direct extraction of cellular material from a tissue sample according to claim 1, wherein said at least one portion of said tissue sample comprises a plurality the different portions of said tissue sample.

3. A method of direct extraction of cellular material from a tissue sample according to claim 1, wherein said adhesive characteristics comprise chemical adhesive properties.

4. A method of direct extraction of cellular material from a tissue sample according to claim 1, wherein said adhesive characteristics comprise electrostatic adhesive properties.

5. A method of direct extraction of cellular material from a tissue sample according to claim 1, wherein said activating comprises applying electromagnetic energy to said region of said transfer surface.

6. A method of direct extraction of cellular material from a tissue sample according to claim 1, wherein said activating comprises applying heat to said region of said transfer surface.

7. A method of direct extraction of cellular material from a tissue sample according to claim 1, wherein said identifying comprises visualizing said tissue sample with a microscope.

8. A method of direct extraction of cellular material from a tissue sample according to claim 7, wherein said identifying and extraction is automated.

9. A method of direct extraction of cellular material from a tissue sample according to claim 1, further comprising analyzing said extracted portion of said tissue sample.

10. A method of direct extraction of cellular material from a tissue sample according to claim 9, wherein said extracted portion of said tissue sample and said activated region of said transfer surface which is adhered thereto are separated from a remaining portion of said transfer surface.

11. A method of direct extraction of cellular material from a tissue sample according to claim 1, wherein said transfer surface comprises a backing layer and an activatable adhesive layer provided on said backing layer.

12. A method of direct extraction of cellular material from a tissue sample according to claim 11, wherein said backing layer is transparent.

13. A method of direct extraction of cellular material from a tissue sample according to claim 11, wherein said backing layer include a label area.

14. A method of direct extraction of cellular material from a tissue sample according to claim 1, wherein said tissue sample comprises a microtome section.

15. A method of direct extraction of cellular material from a tissue sample according to claim 1, wherein said tissue sample comprises a cellular smear.

16. A method of direct extraction of cellular material from a tissue sample according to claim 1, wherein said activating comprises irradiating said region of said transfer surface with laser-derived energy.

* * * * *

UNITED STATES PATENT AND TRADEMARK OFFICE
CERTIFICATE OF CORRECTION

PATENT NO. : 5,843,657
DATED : December 1, 1998
INVENTOR(S) : Lance A. Liotta et al.

It is certified that error appears in the above-identified patent and that said Letters Patent is hereby corrected as shown below:

Title page,
Item [75], Inventor, please add after "Zhongping Zhuang, Bethesda, Md." missing inventor -- Robert F. Bonner. Washington, D.C. --.

Signed and Sealed this

Tenth Day of August, 2004

JON W. DUDAS
*Acting Director of the United States Patent and Trademark Office*